(12) United States Patent
Gustine et al.

(10) Patent No.: US 12,137,948 B2
(45) Date of Patent: Nov. 12, 2024

(54) SPINOUS PROCESS PLATE FIXATION ASSEMBLY

(71) Applicant: NuVasive, Inc., San Diego, CA (US)

(72) Inventors: Seth Gustine, Encinitas, CA (US); Daniel Zatta, Vista, CA (US); Hyun Bae, Santa Monica, CA (US)

(73) Assignee: NuVasive, Inc., San Diego, CA (US)

( * ) Notice: Subject to any disclaimer, the term of this patent is extended or adjusted under 35 U.S.C. 154(b) by 124 days.

(21) Appl. No.: 17/806,595

(22) Filed: Jun. 13, 2022

(65) Prior Publication Data

US 2022/0296282 A1 Sep. 22, 2022

Related U.S. Application Data

(63) Continuation of application No. 16/416,669, filed on May 20, 2019, now Pat. No. 11,382,670, which is a continuation of application No. 15/392,763, filed on Dec. 28, 2016, now Pat. No. 10,335,207.

(60) Provisional application No. 62/273,350, filed on Dec. 30, 2015, provisional application No. 62/272,618, filed on Dec. 29, 2015.

(51) Int. Cl.
*A61B 17/70* (2006.01)

(52) U.S. Cl.
CPC ...... *A61B 17/7068* (2013.01); *A61B 17/7062* (2013.01)

(58) Field of Classification Search
CPC ........ A61F 2/44; A61F 2/4405; A61F 2/4455; A61F 2002/449; A61B 17/7067; A61B 17/7062; A61B 17/7068

USPC ................... 606/246–249; 623/17.11–17.16
See application file for complete search history.

(56) References Cited

U.S. PATENT DOCUMENTS

| 5,167,662 A | 12/1992 | Hayes et al. |
| 5,171,279 A | 12/1992 | Mathews |
| 5,172,011 A | 12/1992 | Leuthold et al. |

(Continued)

FOREIGN PATENT DOCUMENTS

| CN | 201445551 | 5/2010 |
| CN | 201409975 | 1/2014 |

(Continued)

OTHER PUBLICATIONS

U.S. Appl. No. 16/416,669, filed May 20, 2019.

(Continued)

*Primary Examiner* — Eduardo C Robert
*Assistant Examiner* — Tara Rose E Carter

(57) ABSTRACT

A spinous process plate fixation assembly is provided that has a pin plate including a first central aperture and a pin plate interior surface. The assembly has a lock plate including a second central aperture and a lock plate interior surface opposingly facing the pin plate interior surface. The interior surfaces have a pluralities of spikes extending therefrom. A pin receptacle is disposed within the pin plate and is configured to receive a lock pin. A pivoting lock mechanism is disposed within the lock plate. A connector shaft extends from the pin plate to the lock plate and passes through the first central aperture and the second central aperture. The connector shaft includes a pin side configured to receive the lock pin, and a lock side opposite the shaft side, the lock side configured to operatively engage the pivoting lock mechanism so as to secure the plates and the shaft.

19 Claims, 8 Drawing Sheets

(56) References Cited

U.S. PATENT DOCUMENTS

| | | |
|---|---|---|
| 5,291,901 A | 3/1994 | Graf |
| 5,329,933 A | 7/1994 | Graf |
| 5,357,983 A | 10/1994 | Mathews |
| 5,403,316 A | 4/1995 | Ashman |
| 5,470,333 A | 11/1995 | Ray |
| 5,527,314 A | 6/1996 | Brumfield et al. |
| 5,531,745 A | 7/1996 | Ray |
| 5,531,747 A | 7/1996 | Ray |
| 5,534,002 A | 7/1996 | Brumfield et al. |
| 5,562,662 A | 10/1996 | Brumfield et al. |
| 5,609,592 A | 3/1997 | Brumfield et al. |
| 5,645,084 A | 7/1997 | McKay |
| 5,667,506 A | 9/1997 | Sutterlin |
| 5,702,452 A | 12/1997 | Argenson et al. |
| 5,741,261 A | 4/1998 | Moskovitz et al. |
| 5,836,948 A | 11/1998 | Zucherman et al. |
| 5,860,977 A | 1/1999 | Zucherman et al. |
| 5,876,404 A | 3/1999 | Zucherman et al. |
| 5,885,291 A | 3/1999 | Moskovitz et al. |
| 5,885,292 A | 3/1999 | Moskovitz et al. |
| 5,891,147 A | 4/1999 | Moskovitz et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,090,112 A | 7/2000 | Zucherman et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,238,397 B1 | 5/2001 | Zucherman et al. |
| 6,280,444 B1 | 8/2001 | Zucherman et al. |
| 6,312,431 B1 | 11/2001 | Asfora |
| 6,332,882 B1 | 12/2001 | Zucherman et al. |
| 6,332,883 B1 | 12/2001 | Zucherman et al. |
| 6,364,883 B1 | 4/2002 | Santilli |
| 6,379,355 B1 | 4/2002 | Zucherman et al. |
| 6,419,676 B1 | 7/2002 | Zucherman et al. |
| 6,419,677 B2 | 7/2002 | Zucherman et al. |
| 6,451,019 B1 | 9/2002 | Zucherman et al. |
| 6,451,020 B1 | 9/2002 | Zucherman et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,582,433 B2 | 6/2003 | Yun |
| 6,652,527 B2 | 11/2003 | Zucherman et al. |
| 6,652,534 B2 | 11/2003 | Zucherman et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,733,534 B2 | 5/2004 | Sherman |
| 6,764,491 B2 | 7/2004 | Frey et al. |
| 6,796,983 B1 | 9/2004 | Zucherman et al. |
| 6,821,277 B2 | 11/2004 | Teitelbaum |
| 6,899,713 B2 | 5/2005 | Shaolian et al. |
| 6,902,566 B2 | 6/2005 | Zucherman et al. |
| 6,926,728 B2 | 8/2005 | Zucherman et al. |
| 6,949,105 B2 | 9/2005 | Bryan et al. |
| 7,008,424 B2 | 3/2006 | Teitelbaum |
| 7,029,473 B2 | 4/2006 | Zucherman et al. |
| 7,048,736 B2 | 5/2006 | Robinson ......... A61B 17/7068 606/250 |
| 7,101,375 B2 | 9/2006 | Zucherman et al. |
| 7,189,234 B2 | 3/2007 | Zucherman et al. |
| 7,201,751 B2 | 4/2007 | Zucherman et al. |
| 7,220,262 B1 | 5/2007 | Hynes |
| 7,252,673 B2 | 8/2007 | Lim |
| 7,306,628 B2 | 12/2007 | Zucherman et al. |
| 7,335,203 B2 | 2/2008 | Winslow et al. |
| 7,361,193 B2 | 4/2008 | Frey et al. |
| 7,377,942 B2 | 5/2008 | Berry |
| 7,383,639 B2 | 6/2008 | Malandain |
| 7,445,637 B2 | 11/2008 | Taylor |
| 7,473,268 B2 | 1/2009 | Zucherman et al. |
| 7,473,269 B1 | 1/2009 | Hynes |
| 7,476,251 B2 | 1/2009 | Zucherman et al. |
| 7,481,812 B2 | 1/2009 | Frey et al. |
| 7,481,839 B2 | 1/2009 | Zucherman et al. |
| 7,497,024 B2 | 3/2009 | Malandain |
| 7,510,567 B2 | 3/2009 | Zucherman et al. |
| 7,520,887 B2 | 4/2009 | Maxy et al. |
| 7,520,888 B2 | 4/2009 | Trieu |
| 7,524,324 B2 | 4/2009 | Winslow et al. |
| 7,549,999 B2 | 6/2009 | Zucherman et al. |
| 7,550,010 B2 | 6/2009 | Humphreys et al. |
| 7,553,320 B2 | 6/2009 | Molz, IV et al. |
| 7,556,651 B2 | 7/2009 | Humphreys et al. |
| 7,567,834 B2 | 7/2009 | Clayton et al. |
| 7,575,588 B2 | 8/2009 | Barker et al. |
| 7,585,316 B2 | 9/2009 | Trieu |
| 7,588,592 B2 | 9/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,662,187 B2 | 2/2010 | Zucherman et al. |
| 7,666,209 B2 | 2/2010 | Zucherman et al. |
| 7,682,376 B2 | 3/2010 | Trieu |
| 7,691,130 B2 | 4/2010 | Bruneau et al. |
| 7,695,513 B2 | 4/2010 | Zucherman et al. |
| 7,699,873 B2 | 4/2010 | Stevenson et al. |
| 7,727,233 B2 | 6/2010 | Blackwell ......... A61B 17/7068 606/71 |
| 7,749,251 B2 | 7/2010 | Obenchain et al. |
| 7,749,252 B2 | 7/2010 | Zucherman et al. |
| 7,749,253 B2 | 7/2010 | Zucherman et al. |
| 7,758,619 B2 | 7/2010 | Zucherman et al. |
| 7,771,479 B2 | 8/2010 | Humphreys et al. |
| 7,776,069 B2 | 8/2010 | Taylor |
| D623,296 S | 9/2010 | Boyer, II et al. |
| D623,297 S | 9/2010 | Boyer, II et al. |
| 7,794,476 B2 | 9/2010 | Wisnewski |
| 7,803,190 B2 | 9/2010 | Zucherman et al. |
| 7,806,911 B2 | 10/2010 | Peckham |
| 7,824,430 B2 | 11/2010 | Allard et al. |
| 7,828,822 B2 | 11/2010 | Zucherman et al. |
| 7,833,246 B2 | 11/2010 | Mitchell |
| 7,837,688 B2 | 11/2010 | Boyer, II et al. |
| 7,837,711 B2 | 11/2010 | Bruneau et al. |
| 7,846,185 B2 | 12/2010 | Carls et al. |
| 7,857,815 B2 | 12/2010 | Zucherman et al. |
| 7,862,569 B2 | 1/2011 | Zucherman et al. |
| 7,862,590 B2 | 1/2011 | Lim et al. |
| 7,862,591 B2 | 1/2011 | Dewey et al. |
| 7,875,077 B2 | 1/2011 | Humphreys et al. |
| 7,879,104 B2 | 2/2011 | Dewey et al. |
| 7,901,432 B2 | 3/2011 | Zucherman et al. |
| 7,901,459 B2 | 3/2011 | Hodges et al. |
| 7,909,853 B2 | 3/2011 | Zucherman et al. |
| 7,918,875 B2 | 4/2011 | Lins et al. |
| 7,918,877 B2 | 4/2011 | Zucherman et al. |
| 7,922,750 B2 | 4/2011 | Trautwein et al. |
| 7,927,354 B2 | 4/2011 | Edidin et al. |
| 7,931,674 B2 | 4/2011 | Zucherman et al. |
| 7,935,124 B2 | 5/2011 | Frey et al. |
| 7,942,904 B2 | 5/2011 | Thramann et al. |
| 7,953,471 B2 | 5/2011 | Clayton et al. |
| 7,955,356 B2 | 6/2011 | Zucherman et al. |
| 7,955,392 B2 | 6/2011 | Dewey et al. |
| 7,959,652 B2 | 6/2011 | Zucherman et al. |
| 7,972,382 B2 | 7/2011 | Foley et al. |
| 7,985,246 B2 | 7/2011 | Trieu |
| 7,988,709 B2 | 8/2011 | Clark et al. |
| 7,993,342 B2 | 8/2011 | Malandain et al. |
| 7,993,374 B2 | 8/2011 | Zucherman et al. |
| 7,993,404 B2 | 8/2011 | Trieu |
| 7,998,174 B2 | 8/2011 | Malandain et al. |
| 7,998,208 B2 | 8/2011 | Kohm et al. |
| 8,007,517 B2 | 8/2011 | Lins et al. |
| 8,007,521 B2 | 8/2011 | Malandain et al. |
| 8,007,537 B2 | 8/2011 | Zucherman et al. |
| 8,012,209 B2 | 9/2011 | Zucherman et al. |
| 8,021,393 B2 | 9/2011 | Seifert et al. |

(56) References Cited

U.S. PATENT DOCUMENTS

| | | |
|---|---|---|
| 8,029,542 B2 | 10/2011 | Zucherman et al. |
| 8,029,549 B2 | 10/2011 | Malandain et al. |
| 8,029,550 B2 | 10/2011 | Dewey et al. |
| 8,029,567 B2 | 10/2011 | Edidin et al. |
| 8,034,078 B2 | 10/2011 | Laskowitz et al. |
| 8,034,079 B2 | 10/2011 | Bruneau et al. |
| 8,034,080 B2 | 10/2011 | Malandain et al. |
| 8,038,698 B2 | 10/2011 | Edidin et al. |
| 8,043,335 B2 | 10/2011 | Malandain et al. |
| 8,043,336 B2 | 10/2011 | Taylor |
| 8,048,117 B2 | 11/2011 | Zucherman et al. |
| 8,048,118 B2 | 11/2011 | Lim et al. |
| 8,048,119 B2 | 11/2011 | Bruneau et al. |
| 8,057,513 B2 | 11/2011 | Kohm et al. |
| 8,062,337 B2 | 11/2011 | Bruneau et al. |
| 8,066,742 B2 | 11/2011 | Anderson et al. |
| 8,070,778 B2 | 12/2011 | Zucherman et al. |
| 8,083,774 B2 | 12/2011 | Teitelbaum |
| 8,083,795 B2 | 12/2011 | Lange et al. |
| 8,092,459 B2 | 1/2012 | Malandain |
| 8,092,533 B2 | 1/2012 | Melkent |
| 8,092,535 B2 | 1/2012 | Zucherman et al. |
| 8,096,994 B2 | 1/2012 | Phan et al. |
| 8,096,995 B2 | 1/2012 | Kohm et al. |
| 8,097,018 B2 | 1/2012 | Malandain et al. |
| 8,097,019 B2 | 1/2012 | Mitchell et al. |
| 8,100,943 B2 | 1/2012 | Malandain et al. |
| 8,100,945 B2 | 1/2012 | Dewey et al. |
| 8,105,357 B2 | 1/2012 | Bruneau et al. |
| 8,109,972 B2 | 2/2012 | Zucherman et al. |
| 8,114,136 B2 | 2/2012 | Carls et al. |
| 8,118,844 B2 | 2/2012 | Anderson et al. |
| 8,128,659 B2 | 3/2012 | Ginsberg et al. |
| 8,128,663 B2 | 3/2012 | Zucherman et al. |
| 8,128,702 B2 | 3/2012 | Zucherman et al. |
| 8,226,653 B2 | 7/2012 | Blackwell et al. |
| 8,241,330 B2 | 8/2012 | Lamborne et al. |
| 8,343,190 B1 | 1/2013 | Mueller et al. |
| 8,382,801 B2 | 2/2013 | Lamborne et al. |
| 8,419,738 B2 | 4/2013 | Smisson, III et al. |
| 8,439,951 B2 | 5/2013 | Trautwein et al. |
| 8,439,953 B2 | 5/2013 | Mitchell et al. |
| 8,449,577 B2 | 5/2013 | Kloss .................. A61B 17/704 606/264 |
| 2001/0021850 A1 | 9/2001 | Zucherman et al. |
| 2001/0031965 A1 | 10/2001 | Zucherman et al. |
| 2002/0099377 A1 | 7/2002 | Zucherman et al. |
| 2002/0111679 A1 | 8/2002 | Zucherman et al. |
| 2002/0143331 A1 | 10/2002 | Zucherman et al. |
| 2004/0153071 A1 | 8/2004 | Zucherman et al. |
| 2005/0075634 A1 | 4/2005 | Zucherman et al. |
| 2005/0101955 A1 | 5/2005 | Zucherman et al. |
| 2005/0143738 A1 | 6/2005 | Zucherman et al. |
| 2005/0154392 A1 | 7/2005 | Medoff .............. A61B 17/8047 606/287 |
| 2005/0228383 A1 | 10/2005 | Zucherman et al. |
| 2005/0228384 A1 | 10/2005 | Zucherman et al. |
| 2005/0245937 A1 | 11/2005 | Winslow |
| 2006/0036258 A1 | 2/2006 | Zucherman et al. |
| 2006/0184248 A1 | 8/2006 | Edidin et al. |
| 2006/0195102 A1 | 8/2006 | Malandain |
| 2006/0235386 A1 | 10/2006 | Anderson |
| 2006/0235521 A1 | 10/2006 | Zucherman et al. |
| 2006/0247623 A1 | 11/2006 | Anderson et al. |
| 2006/0247634 A1* | 11/2006 | Warner .............. A61B 17/7062 606/279 |
| 2006/0247773 A1 | 11/2006 | Stamp |
| 2006/0264939 A1 | 11/2006 | Zucherman et al. |
| 2006/0271048 A1 | 11/2006 | Thramann |
| 2006/0271055 A1 | 11/2006 | Thramann |
| 2006/0271194 A1 | 11/2006 | Zucherman et al. |
| 2007/0005064 A1 | 1/2007 | Anderson et al. |
| 2007/0043360 A1 | 2/2007 | Thramann |
| 2007/0073293 A1 | 3/2007 | Martz et al. |
| 2007/0168039 A1 | 7/2007 | Trieu |
| 2007/0173821 A1 | 7/2007 | Trieu |
| 2007/0173822 A1 | 7/2007 | Bruneau et al. |
| 2007/0191838 A1 | 8/2007 | Bruneau et al. |
| 2007/0213717 A1 | 9/2007 | Trieu et al. |
| 2007/0213718 A1 | 9/2007 | Trieu |
| 2007/0213823 A1 | 9/2007 | Trieu |
| 2007/0213824 A1 | 9/2007 | Trieu |
| 2007/0227547 A1 | 10/2007 | Trieu |
| 2007/0233068 A1 | 10/2007 | Bruneau et al. |
| 2007/0233074 A1 | 10/2007 | Anderson et al. |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270829 A1 | 11/2007 | Carls et al. |
| 2007/0276496 A1 | 11/2007 | Lange et al. |
| 2007/0276497 A1 | 11/2007 | Anderson |
| 2008/0021460 A1 | 1/2008 | Bruneau et al. |
| 2008/0021468 A1 | 1/2008 | Zucherman et al. |
| 2008/0027434 A1 | 1/2008 | Zucherman et al. |
| 2008/0027435 A1 | 1/2008 | Zucherman et al. |
| 2008/0027545 A1 | 1/2008 | Zucherman et al. |
| 2008/0039859 A1 | 2/2008 | Zucherman et al. |
| 2008/0046086 A1 | 2/2008 | Zucherman et al. |
| 2008/0051904 A1 | 2/2008 | Zucherman et al. |
| 2008/0051905 A1 | 2/2008 | Zucherman et al. |
| 2008/0058941 A1 | 3/2008 | Zucherman et al. |
| 2008/0071280 A1 | 3/2008 | Winslow |
| 2008/0071378 A1 | 3/2008 | Zucherman et al. |
| 2008/0082118 A1 | 4/2008 | Edidin et al. |
| 2008/0082167 A1 | 4/2008 | Edidin et al. |
| 2008/0086212 A1 | 4/2008 | Zucherman et al. |
| 2008/0097433 A1 | 4/2008 | Molz |
| 2008/0108990 A1 | 5/2008 | Mitchell et al. |
| 2008/0114358 A1 | 5/2008 | Anderson et al. |
| 2008/0114455 A1 | 5/2008 | Lange et al. |
| 2008/0114456 A1 | 5/2008 | Dewey et al. |
| 2008/0147192 A1 | 6/2008 | Edidin et al. |
| 2008/0161856 A1 | 7/2008 | Liu et al. |
| 2008/0167685 A1 | 7/2008 | Allard et al. |
| 2008/0177298 A1 | 7/2008 | Zucherman et al. |
| 2008/0183210 A1 | 7/2008 | Zucherman et al. |
| 2008/0183211 A1 | 7/2008 | Lamborne ............ A61B 17/842 606/249 |
| 2008/0183218 A1 | 7/2008 | Mueller et al. |
| 2008/0195159 A1 | 8/2008 | Kloss .................. A61B 17/7037 606/305 |
| 2008/0215058 A1 | 9/2008 | Zucherman et al. |
| 2008/0243250 A1 | 10/2008 | Seifert et al. |
| 2008/0281359 A1 | 11/2008 | Abdou |
| 2008/0281360 A1 | 11/2008 | Vittur et al. |
| 2008/0281361 A1 | 11/2008 | Vittur et al. |
| 2008/0294199 A1 | 11/2008 | Kohm et al. |
| 2008/0294200 A1 | 11/2008 | Kohm et al. |
| 2009/0198277 A1 | 8/2009 | Gordon et al. |
| 2009/0248081 A1 | 10/2009 | LeHuec et al. |
| 2009/0265006 A1 | 10/2009 | Seifert et al. |
| 2010/0030285 A1 | 2/2010 | Dewey et al. |
| 2010/0042150 A1 | 2/2010 | Anderson |
| 2010/0042151 A1 | 2/2010 | Anderson |
| 2010/0087869 A1 | 4/2010 | Abdou |
| 2010/0094344 A1 | 4/2010 | Trieu |
| 2010/0114320 A1 | 5/2010 | Lange et al. |
| 2010/0145387 A1 | 6/2010 | Bruneau et al. |
| 2010/0150881 A1 | 6/2010 | Thramann |
| 2010/0152780 A1 | 6/2010 | Stevenson et al. |
| 2010/0217320 A1 | 8/2010 | Landis |
| 2010/0241166 A1 | 9/2010 | Dwyer et al. |
| 2010/0241167 A1 | 9/2010 | Taber et al. |
| 2010/0241169 A1 | 9/2010 | Lin et al. |
| 2010/0249841 A1 | 9/2010 | Trieu et al. |
| 2010/0268277 A1 | 10/2010 | Bruneau et al. |
| 2010/0324601 A1 | 12/2010 | Allard et al. |
| 2011/0022090 A1 | 1/2011 | Anderson et al. |
| 2011/0022091 A1 | 1/2011 | Anderson et al. |
| 2011/0029020 A1 | 2/2011 | Gordon et al. |
| 2011/0054531 A1 | 3/2011 | Lamborne et al. |
| 2011/0066186 A1 | 3/2011 | Lee et al. |
| 2011/0125191 A1 | 5/2011 | Lee et al. |
| 2011/0130836 A1 | 6/2011 | Thramann et al. |

(56) References Cited

U.S. PATENT DOCUMENTS

| | | |
|---|---|---|
| 2011/0160772 A1 | 6/2011 | Arcenio et al. |
| 2011/0166600 A1 | 7/2011 | Lamborne et al. |
| 2011/0172720 A1 | 7/2011 | Metcalf, Jr. et al. |
| 2011/0184468 A1 | 7/2011 | Metcalf, Jr. et al. |
| 2011/0213418 A1 | 9/2011 | Trieu et al. |
| 2011/0218633 A1 | 9/2011 | Frey et al. |
| 2011/0238114 A1 | 9/2011 | Lim et al. |
| 2011/0270402 A1 | 11/2011 | Frey et al. |
| 2011/0295373 A1 | 12/2011 | Foley et al. |
| 2011/0307010 A1* | 12/2011 | Pradhan .............. A61B 17/7062 606/249 |
| 2011/0319936 A1 | 12/2011 | Gordon et al. |
| 2012/0059422 A1 | 3/2012 | Esce |
| 2012/0065684 A1 | 3/2012 | Anderson |
| 2012/0089184 A1 | 4/2012 | Yeh |
| 2012/0089194 A1 | 4/2012 | Strausbaugh ...... A61B 17/7038 606/301 |
| 2012/0101528 A1 | 4/2012 | Souza et al. |
| 2012/0109198 A1 | 5/2012 | Dryer et al. |
| 2012/0109203 A1 | 5/2012 | Dryer et al. |
| 2012/0143252 A1 | 6/2012 | Robinson |
| 2012/0215262 A1* | 8/2012 | Culbert .............. A61B 17/8625 606/279 |
| 2012/0221051 A1 | 8/2012 | Robinson ........... A61B 17/7068 606/249 |
| 2012/0265204 A1 | 10/2012 | Schmierer et al. |
| 2013/0012996 A1 | 1/2013 | Zamani et al. |
| 2013/0030467 A1 | 1/2013 | Karas et al. |
| 2013/0060284 A1 | 3/2013 | Abdou |
| 2013/0090689 A1 | 4/2013 | Villavicencio |
| 2013/0103086 A1 | 4/2013 | Marik et al. |
| 2013/0103088 A1 | 4/2013 | Karahalios et al. |
| 2013/0184707 A1 | 7/2013 | Mirza .............. A61B 17/8052 606/59 |
| 2013/0184751 A1 | 7/2013 | Siegfried |
| 2013/0184752 A1 | 7/2013 | Binder ............... A61B 17/7068 606/248 |
| 2013/0184753 A1 | 7/2013 | Keiper et al. |
| 2013/0184754 A1 | 7/2013 | Taber et al. |
| 2013/0190820 A1 | 7/2013 | Siegfried et al. |
| 2013/0197581 A1 | 8/2013 | Justis et al. |
| 2013/0253585 A1 | 9/2013 | Garcia et al. |
| 2013/0304137 A1 | 11/2013 | Zappacosta et al. |
| 2014/0012338 A1 | 1/2014 | Kirschman |
| 2015/0327891 A1* | 11/2015 | Brahm ............... A61B 17/7067 606/279 |
| 2019/0269442 A1 | 9/2019 | Gustine et al. |

FOREIGN PATENT DOCUMENTS

| | | |
|---|---|---|
| DE | 3113142 | 1/1982 |
| EP | 2468202 | 6/2012 |
| FR | 2816197 | 5/2002 |
| KR | 20060036760 | 5/2006 |
| KR | 101030462 | 4/2011 |
| KR | 101306942 | 9/2013 |
| KR | 20130108788 | 10/2013 |
| RU | 9378 | 3/1999 |
| WO | WO2006065932 | 6/2006 |
| WO | WO2006102269 | 9/2006 |
| WO | WO2008086533 | 7/2008 |
| WO | WO2010114925 | 10/2010 |
| WO | WO2011019721 | 2/2011 |
| WO | WO2011019756 | 2/2011 |
| WO | WO2013130907 | 9/2013 |
| WO | WO200018311 | 10/2013 |
| WO | WO200128469 | 10/2013 |
| WO | WO2013159097 | 10/2013 |

OTHER PUBLICATIONS

U.S. Appl. No. 15/392,763, filed Dec. 28, 2016.
U.S. Appl. No. 62/273,350, filed Dec. 30, 2015.
U.S. Appl. No. 62/272,618, filed Dec. 29, 2015.

* cited by examiner

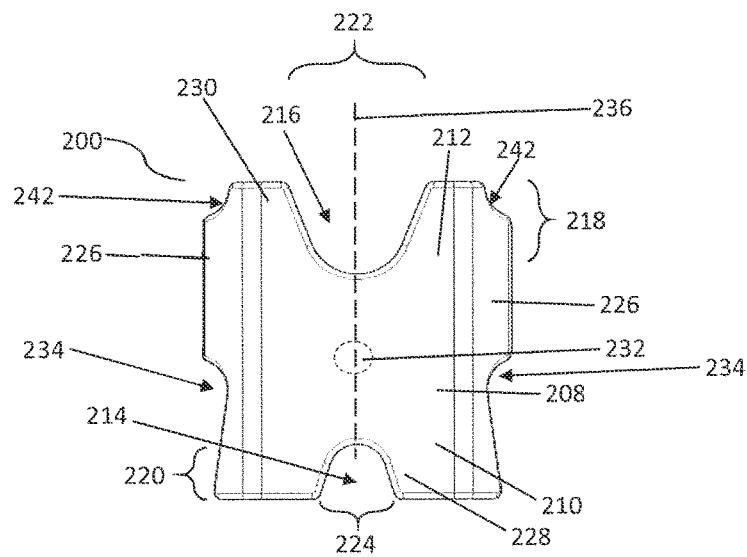
FIG. 21A
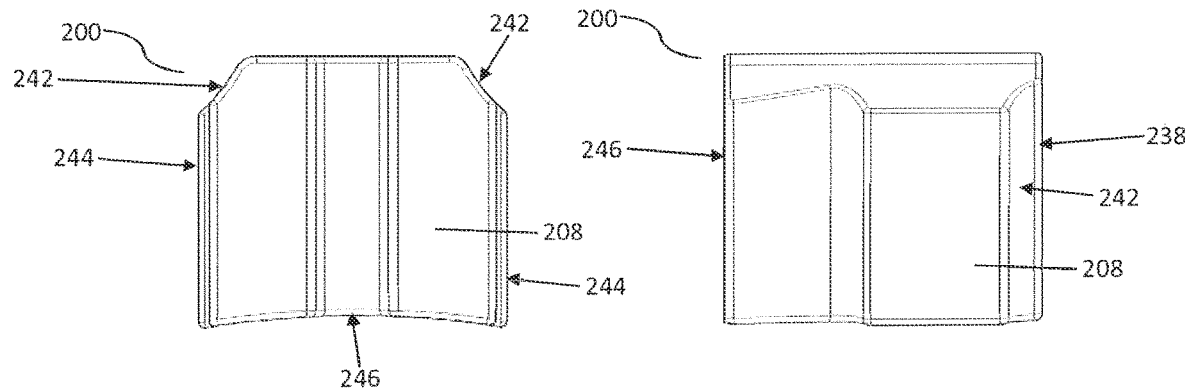
FIG. 21B
FIG. 21C

SPINOUS PROCESS PLATE FIXATION ASSEMBLY

CROSS REFERENCE TO RELATED APPLICATIONS

The present application is a continuation of U.S. patent application Ser. No. 16/416,669 filed on May 20, 2019, which claims priority to U.S. patent application Ser. No. 15/392,763 filed Dec. 28, 2016, which claims priority to U.S. Provisional Application No. 62/272,618, filed on Dec. 29, 2015, and U.S. Provisional Application No. 62/273,350, filed on Dec. 30, 2015, each of which is entirely incorporated herein by reference.

FIELD

The present disclosure relates generally to medical devices, more specifically to the field of spinal surgery and devices for fusing adjacent spinous processes to stabilize the vertebral segment associated with the particular spinous processes. Such devices as well as systems and methods for use therewith are described.

BACKGROUND

The spinal column is critical in human physiology for mobility, support, and balance. The spine column protects the nerves of the spinal cord, which convey commands from the brain to the rest of the body, and convey sensory information from the nerves below the neck to the brain. The spinal column is made of two basic components—vertebrae (bone) and intervertebral discs (gel-like cushions that absorb pressure and prevent vertebrae from rubbing together). A number of vertebrae and intervertebral discs stack together to form a column that provides support and structure for the body while still allowing a large degree of motion and flexibility and protecting the spinal cord. Even minor spinal injuries can be debilitating to the patient, and major spinal injuries can be catastrophic. The loss of the ability to bear weight or permit flexibility can immobilize the patient. Even in less severe cases, small irregularities in the spine can put pressure on the nerves connected to the spinal cord, causing devastating pain and loss of coordination. Examples of causes of such pain include changes in disc height and improper motion of vertebrae.

Surgical procedures on the spine often include the immobilization of two or more vertebrae, typically by fusing vertebrae together. As a result of such surgical invention, disc height may be corrected, and vertebrae may be immobilized, while fusion occurs.

One of the more common methods for achieving the desired immobilization is through the application of bone anchors (most often introduced into the pedicles associated with the respective vertebrae to be fixed) that are then connected by rigid rods locked to each pedicle screw. A significant challenge with such bone anchors is securing the pedicle screws without breaching, cracking, or otherwise compromising the pedicle wall, which may occur if the screw is not properly aligned with the pedicle axis. Moreover, such pedicle screw systems require invasive surgery. Therefore, a need continues to exist for systems for fusing vertebrae that can be used as alternatives to pedicle screws and can be used in minimally invasive surgical procedures.

SUMMARY

The needs described above, as well as others, are addressed by embodiments of a spinous process plate fixation assembly described in this disclosure (although it is to be understood that not all needs described above will necessarily be addressed by any one embodiment), as the spinous process fixation plate assembly of the present disclosure is separable into multiple pieces and can be assembled in-situ, and thus, can be used in minimally invasive spinal surgeries. Moreover, the assembly of the present disclosure does not rely on a pedicle screw system.

In an aspect, a spinous process plate fixation assembly includes a pin plate and a lock plate. The pin plate has a first central aperture and a pin plate interior surface. The pin plate interior surface has a first plurality of spikes extending therefrom. A pin receptacle is disposed within the pin plate and is configured to receive a lock pin. The lock plate has a second central aperture and a lock plate interior surface opposingly facing the pin plate interior surface. The lock plate interior surface has a second plurality of spikes extending therefrom. A pivoting lock mechanism is disposed within the lock plate. A connector shaft extends from the pin plate to the lock plate and passes through the first central aperture and the second central aperture. The connector shaft includes a pin side configured to receive the lock pin, and a lock side opposite the shaft side, the lock side configured to operatively engage the pivoting lock mechanism.

In an embodiment of the spinous process plate fixation assembly, the lock mechanism includes a threaded channel disposed within a top surface of the lock plate and a lock chamber disposed within the lock plate. A pivoting lock is disposed within the lock chamber and includes a lock slot in communication with the threaded channel. The pivoting lock includes a connector shaft passage configured to receive the lock side of the connector shaft.

In an embodiment of the spinous process plate fixation assembly, each of the first plurality of spikes and the second plurality of spikes include spikes having cuboid-shaped bases and pyramid-shaped tips. The first and second pluralities of spikes may be positioned on offset flat portions of the pin plate and the lock plate, respectively. Each of the pin plate and the lock plate may have two staggered flat portions.

The pin plate and the lock plate may each include an exterior face positioned opposite of the pin plate interior surface and the lock plate interior surface, respectively. Each of the exterior faces may include at least two compressor alignment slots disposed on opposite sides of the connector shaft.

In another aspect, a kit comprises a lock pin and a pin plate including a first central aperture and a shaft plate interior surface, the pin plate interior surface including a first plurality of spikes. A pin receptacle is disposed within the pin plate and configured to receive the lock pin. The lock plate includes a second central aperture and a lock plate interior surface. The lock plate interior surface including a second plurality of spikes. The kit includes a pivoting lock mechanism configured to be received in the lock plate. The kit comprises a connector shaft configured to extend from the pin plate to the lock plate and pass through the first central aperture and the second central aperture. The connector shaft includes a pin side configured to receive the lock pin; and a lock side opposite the shaft side, the lock side configured to operatively engage the pivoting lock mechanism.

The pivoting lock mechanism may include a threaded channel disposed within a top surface of the lock plate, a lock chamber disposed within the lock plate, and a pivoting lock disposed within the lock chamber and including a lock slot in communication with the threaded channel. In an embodiment, the pivoting lock includes a connector shaft passage configured to receive the lock side of the connector shaft. The pivoting lock may include an exterior toroidal surface and an interior friction fit surface. In some embodiments, the kit includes a lock flange configured to secure the pivoting lock within the lock chamber. The pivoting lock may include a compression slot proximal to the lock slot and opposite from a compression flat configured for orientation when the pivoting lock is compressed. The compression slot may be configured to be reduced when the pivoting lock is compressed.

In an embodiment of the kit, each of the pin plate and the lock plate include at least two staggered flat portions. Each of the pin plate and the lock plate may include an exterior face opposite of the pin plate interior surface and the lock plate interior surface, respectively. Each of the exterior faces may include at least two compressor alignment slots disposed on opposite sides of the connector shaft. The kit may include an instrument selected from the group of an inserter-compressor instrument, a shaft inserter, a single locking tool, a compressor, and combinations thereof.

In another aspect, a midline spinal allograft includes a body having a lower side opposite of an upper side. The lower side has a caudal groove dimensioned to receive a cranial side of a lower spinous process. The upper side has a cranial groove dimensioned to receive a cranial side of an upper spinous process. The cranial groove may have a cranial groove height greater than a caudal groove height of the caudal groove, and the cranial groove may have a cranial groove width greater than a caudal groove width of the caudal groove. At least two lower legs are disposed around the caudal groove, and at least two upper legs are disposed around the cranial groove.

In yet another aspect, a method of producing a demineralized allograft is disclosed herein. The method includes harvesting cancellous bone, cutting the harvested cancellous bone into a predetermined block size, weighing the cut cancellous bone, determining the cut cancellous bone has a mass density greater than a minimum mass density, shaping and sizing the cut cancellous bone to a predetermined shape and size to form a midline spinous allograft, washing the midline spinous allograft, demineralizing the midline spinous allograft in an acid, cleaning the demineralized midline spinous allograft, and packaging the cleaned demineralized midline spinous allograft.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 21A A top view of the midline allograft of FIG. 20.

FIG. 21B A bottom view of the midline allograft of FIG. 20.

FIG. 21C A side view of the midline allograft of FIG. 20.

DETAILED DESCRIPTION

Illustrative embodiments of a spinous process plate fixation assembly and midline spinous process allograft are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinous process fixation plate assembly, midline spinous process allograft, and related methods disclosed herein boast a variety of inventive features and components that warrant patent protection, both individually and in combination.

As used herein, the term "proximal" means the side facing closest to the surgeon when the device is properly implanted, whereas the term "distal" means the side facing away from the surgeon.

Spinous Process Plate Fixation Assembly

Figure 4:
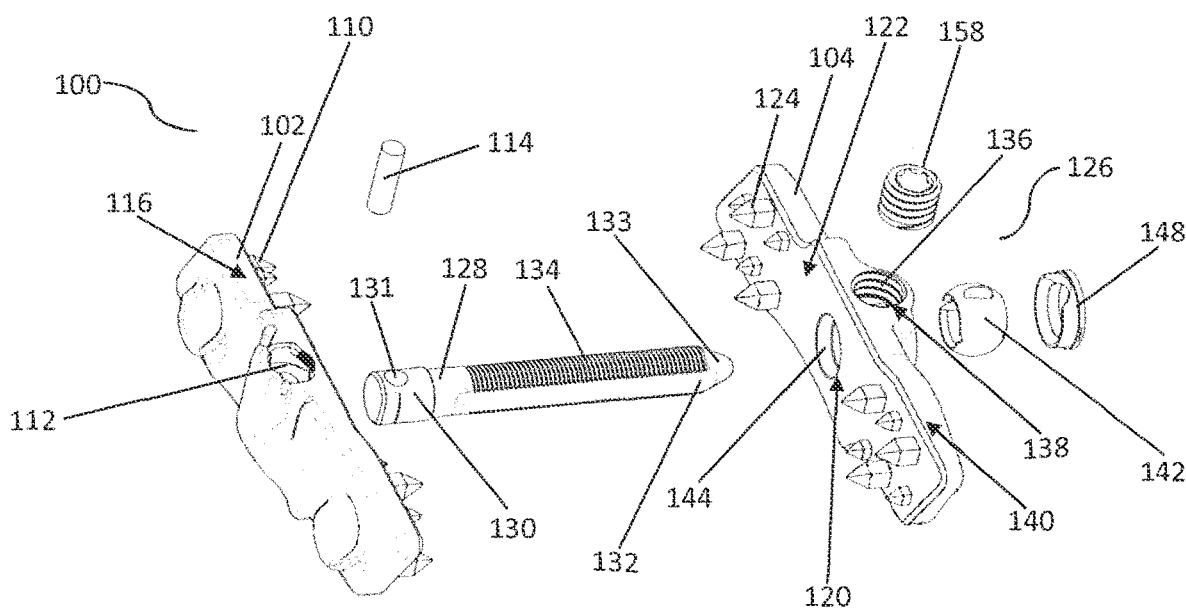
FIG. 4 An exploded view of the spinous process plate fixation assembly shown in FIG. 1.

A spinous process plate fixation assembly 100 is provided that includes a pin plate 102 and a lock plate 104. The pin plate 102 has a first central aperture 106 disposed at, or proximate to, the center of a pin plate interior surface 108. The pin plate interior surface 108 may be flat or substantially flat. The pin plate interior surface 108 has a first plurality of spikes 110 extending therefrom. A pin receptacle 112 is disposed within the pin plate 102 and is configured to receive a lock pin 114 (FIG. 4). The pin receptacle 112 may originate in a top surface 116 of the pin plate 102. The pin receptacle 112 may include a pin chamber 118 that is shaped complementarily to pin 114 such as to receive the pin 114. The pin chamber 118 may extend vertically through the pin plate 102.

Figure 1:
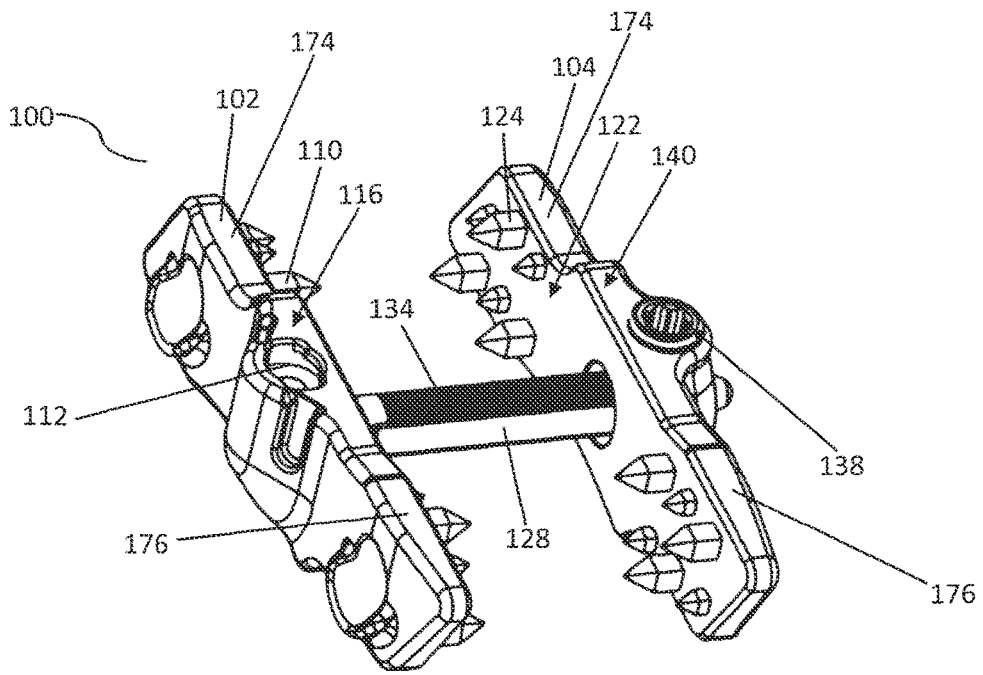
FIG. 1 A perspective view of an embodiment of a spinous process plate fixation assembly as assembled for usage.
Figure 2:
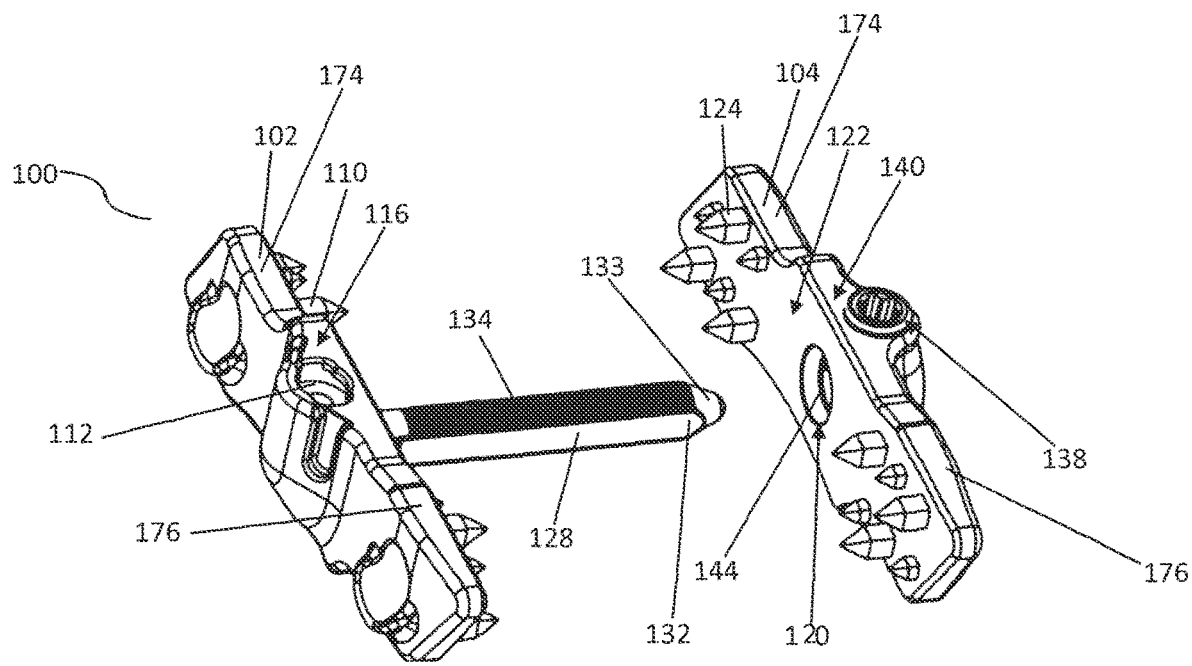
FIG. 2 A perspective view of the spinous process plate fixation assembly shown in FIG. 1 when disassociated.

When joined in the spinous process plate fixation assembly 100 (as shown in FIG. 1), the lock plate 104 may be positioned laterally opposite of the pin plate 102. The lock plate 104 has a second central aperture 120 disposed at, or proximate to, the center of a lock plate interior surface 122. The lock plate interior surface 122 opposingly faces the pin plate interior surface 108 when the assembly 100 is assembled. The lock plate interior surface 122 has a second plurality of spikes 124 extending therefrom. A pivoting lock mechanism 126 is disposed within the lock plate 104. The pivoting lock mechanism 126 may be in fluid communication with the second central aperture 120. When assembler 100 is assembled, a connector shaft 128 extends from the pin plate 102 to the lock plate 104 and passes through the first central aperture 106 and the second central aperture 120, operatively connecting the pin plate 102 and the lock plate 104, as shown in FIG. 1.

The connector shaft 128 includes a pin side 130 configured to receive the lock pin 114, and a lock side 132 opposite the pin side 130, the lock side 132 being configured to operatively engage the pivoting lock mechanism 126. The pin side 130 may have a pin lock channel 131 disposed vertically therein that is configured to receive the lock pin 114. The pin lock channel 131 may be shaped complementary to the lock pin 114. In one embodiment of the assembly 100, the pin 114 is welded, or otherwise fixedly attached, to the pin plate 102 such that the pin 114 is secured within both of the pin lock channel 131 of the connector shaft 128 and the pin receptacle 112 of the pin plate 102. The welding or attachment of pin 114 fixes the connection between the pin plate 102 and the connector shaft 128 such that the connector shaft 128 does not move relative to the pin 114. In an alternative embodiment of the assembly 100, the pin 114 is not welded or fixedly attached to the pin plate 102 such that the connector shaft 128 is able to move relative to the pin 114.

The lock side 132 of the connector shaft 128 may include a tapered tip 133. When engaged in the lock plate assembly 100, the tapered tip 133 may extend beyond the outer most surface of the lock plate 104. Advantageously, the tapered tip 133 enables user-friendly engagement for a surgeon assembling the assembly 100 in-situ. For example, the tapered tip 133 allows the surgeon to easily position the tapered tip 133 with a pre-perforated ligament (not shown) or to create a perforation (not shown) using the tapered tip 133. The connector shaft 128 may have a plurality of flanges 134, which may be V-shaped, disposed on its surface for operatively engaging pivoting lock mechanism 126. The V-shaped flanges 134 increase friction during locking of the assembly 100 due to an interaction with the pivoting lock mechanism 126 and a lock groove 156.

Figure 3:
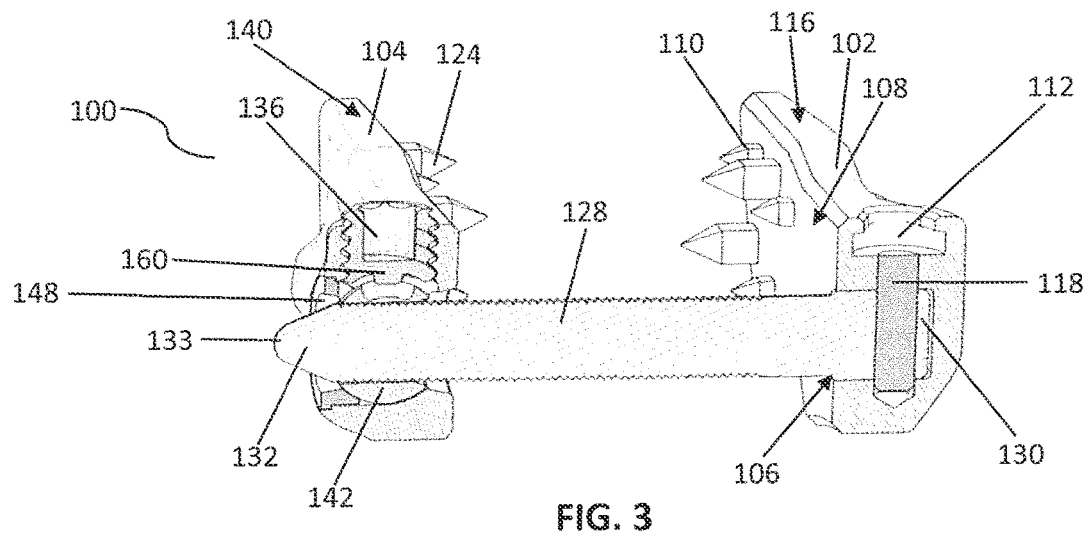
FIG. 3 A cross-section view of the spinous process plate fixation assembly shown in FIG. 1.

In an embodiment, as shown in FIGS. 3 and 4, the pivoting lock mechanism 126 includes a threaded channel 136 disposed vertically through the lock plate 104 and terminating at a lock aperture 138 in a top surface 140 of the lock plate 104. The lock aperture 138 is open to the threaded channel 136. A pivoting lock 142, shown in detail in FIG. 5, can be disposed in a lock chamber 144 of the lock plate 104 when assembled (as shown in, for example, FIG. 3) as part of the pivoting lock mechanism 126. The pivoting lock 142 includes a lock slot 145 that is in fluid communication with the threaded channel 136 of the lock plate 104 when the assembly 100 is assembled (FIG. 3). The pivoting lock 142 includes a connector shaft passage 146 configured to receive the lock side 132 of the connector shaft 128. The pivoting lock mechanism 126 includes a lock flange 148 which is configured to be received by the lock chamber 144, the connector shaft 128, and the pivoting lock 142. When the assembly 100 is assembled, as shown in FIGS. 1 and 3, the lock flange 148 secures the pivoting lock 142 within the lock chamber 144 of the lock plate 104 while allowing the pivoting lock 142 to pivot, or rotate, within the lock chamber 144.

Figure 5:
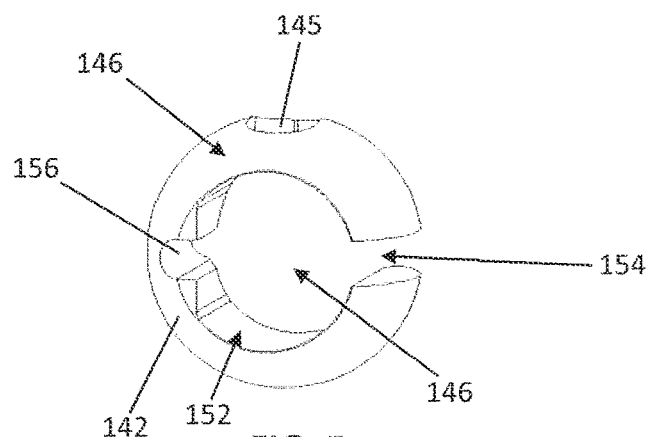
FIG. 5 A perspective view of the pivoting lock of the spinous process place assembly shown in FIG. 1.

As shown in FIG. 5, the pivoting lock 142 may have an exterior toroidal surface 150. The exterior toroidal surface 150 may be shaped complementary to the lock chamber 144 so that the pivoting lock 142 can be received and rotate within the chamber 144. The pivoting lock 142 may have an interior friction fit surface 152. The interior friction fit surface 152 may be shaped complementary to the shape of the connector shaft 128. As such, the shape of the friction fit surface 152 is laterally flat and has two arcs that continuously curve, interrupted by a compression slot 154 and the lock groove 156. The compression slot 154 may be positioned proximate to the lock slot 145, and the lock groove 156 may be positioned opposite of lock groove 156. Advantageously, when the pivoting lock 142 is compressed in use, the compression slot 154 is reduced, or pinches, to enable the pivoting lock 142 to secure the connector shaft 128 that is disposed within the connector shaft passage 146. The lock groove 156 provides flexibility in the axis of the reduction such that the compression slot 154 is reduced when vertical force is applied in use. This force may be applied by a threaded locking feature 158.

The threaded locking feature 158 may have threads configured to operatively engage with threads in the threaded channel 136 of the lock plate 104. When the threaded locking feature 158 is engaged with the threaded channel 136, the threaded locking feature 158 travels through the threaded channel 136 to engage and secure the pivoting lock 142. The threaded locking feature 158 may have a locking tab 160 disposed on its base, the locking tab 160 configured to engage with the locking slot 145 of the pivoting lock 142. Advantageously, when the threaded locking feature 158 engages and secures the pivoting lock 142, the pivoting lock 142 is fixed, or secured, in a position, thereby also securing the lock side 132 of the connector shaft 128.

Advantageously, the pivoting lock mechanism 126 disclosed herein allows the assembly 100 to have nearly infinite variable locking positions with the maximum positions formed by the threaded locking feature 158 and the lock plate 104. The pivoting lock mechanism 126 allows the lock plate 104 to float around it prior to locking. During compression, the pivoting lock mechanism 126 allows the lock plate 104 to articulate in all directions, and then during locking secures the lock plate 104 in the position found during compression. The compression on the pivoting lock 142 remains the same in any position.

In an embodiment of the assembly 100, each of the first plurality of spikes 110 and the second plurality of spikes 124 include spikes having cuboid-shaped bases 162 and pyramid-shaped tips 164 (FIGS. 9 and 10) (which can be described as "house-shaped"). Each of the first plurality of spikes 110 and the second plurality of spikes 124 may have minor (i.e., relatively small) spikes 166 and major (i.e., relatively large) spikes 168. The house-shaped spikes of varying size increase the bite, or grip, of the spikes on vertebrae 170 of a spine 172 to be immobilized and provide increased resistance, when engaged with the vertebrae 170, of movement, including caudal, cranial, distal, dorsal and rotational. In particular, engaged pluralities of spikes 110 and 124 provide a high level of torsional micro motion resistance within the bone during flexion/extension movement. The first plurality of spikes 110 and the second pluralities of spikes 124 may each be positioned on a first offset flat portion 174 and a second offset flat portion 176, respectively, of the plates 102 and 104. Each of the pin plate 102 and the lock plate 104 may have exactly two staggered flat portions 174 and 176. The first offset flat portion 174 and the second offset flat portion 176 may be vertically offset, or staged, from one another around the connector shaft 128. The first flat portion 174 may be defined by a step-down, or drop, in a bottom surface 178 in the pin plate 102 and a bottom surface 180 in the lock plate 104, and a step-down, or drop in the top surfaces 116 and 140 of the plates 102 and 104. The second flat portion 176 may be positioned opposite from the first flat portion 174. The second flat portion 176 may be defined by a step-up, or rise, in a bottom surface 178 in the pin plate 102 and a bottom surface 180 in the lock plate 104, and a step-up, or rise in the top surfaces 116 and 140 of the plates 102 and 104. The top surfaces 116 and 140 and the bottom surfaces 178 and 180 are flat, or substantially flat, across the first offset flat portion 174 and the second offset flat portion 176.

Advantageously, assembly 100 having plates 102 and 104 with flat portions 174 and 176 has a lower profile, which is beneficial for performing minimally invasive surgeries, and is shaped to interface with allograft and/or polyetheretherketone devices. The anterior side of the plates 102 and 104 can include a radiused section 177 configured to interact with the allograft or a polyetheretherketone spacer. The dimensions of the radiused section 177 allow the assembly 100 to be post packed with autograft or allograft after full locking, as the connector shaft 128 and the interior surfaces 108 and 122 create a barrier with which bone chips can easily be packed. Moreover, the lower profile of the disclosed assembly 100 allows the plates 102 and 104 to attach further on a spinous process 194 and to have the pluralities of spikes 110 and 124 compressed into the transition area between the lamina and the spinous process 194. Furthermore, this profile potentially enables multi-level fixation of vertebrae 170.

Figure 9:
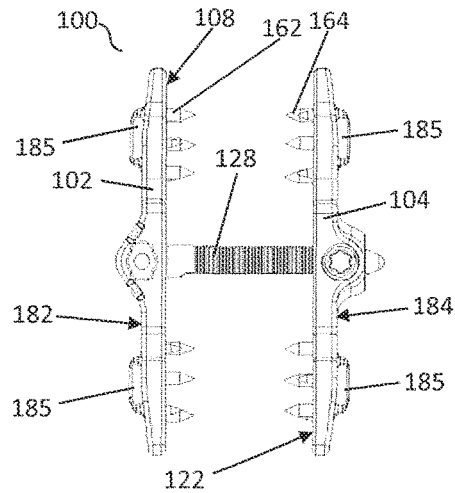
FIG. 9 A top view of the spinous process plate fixation assembly shown in FIG. 1.
Figure 10:
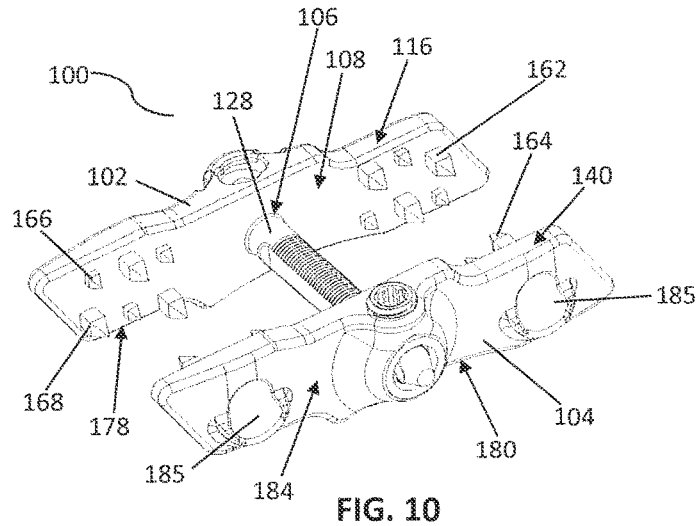
FIG. 10 An alternate perspective view of the spinous process plate fixation assembly shown in FIG. 1.
Figure 11:
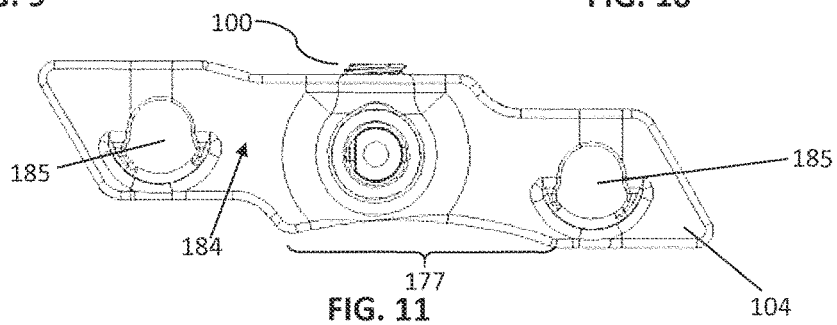
FIG. 11 A side view of the spinous process plate fixation assembly shown in FIG. 1.

The pin plate 102 and the lock plate 104 may include a pin plate exterior face 182 and a lock plate exterior face 184, respectively (FIG. 9). The pin plate exterior face 182 is positioned opposite of the pin plate interior surface 108 on the pin plate 102, and the lock plate exterior face 184 is positioned opposite of the lock plate interior surface 122 on the lock plate 104. The at least two compressor alignment slots 185 may be disposed on opposite sides around the connector shaft 128. Each of the exterior faces 182 and 184 may include at least two compressor alignment slots 185 that extend partially into the exterior faces 182 and 184.

Figure 12:
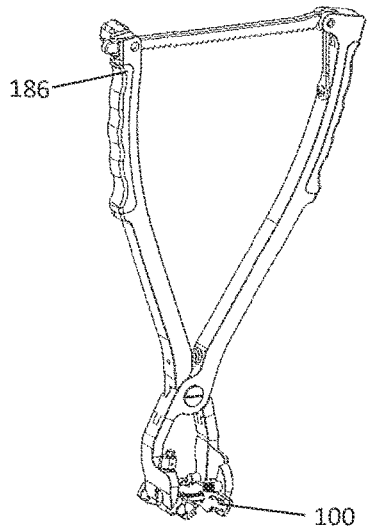
FIG. 12 A perspective view of a combination inserter-compressor instrument holding an assembled spinous process plate fixation assembly shown in FIG. 1.

As shown in FIGS. 12-16, various tools may engage with the assembly 100 and be utilized in use of the assembly 100. For example, as shown in FIG. 12, an embodiment of the assembly 100 can be associated with a combination inserter-compressor instrument 186. The combination inserter-compressor instrument 186 is configured to simultaneously engage the at least two compressor slots 185 while inserting the lock pin 114 into the pin receptacle 112 and the threaded locking feature 158 into the threaded channel 136 when the assembly 100 is positioned in a subject, such as a human, during spinal surgery.

Figure 13:
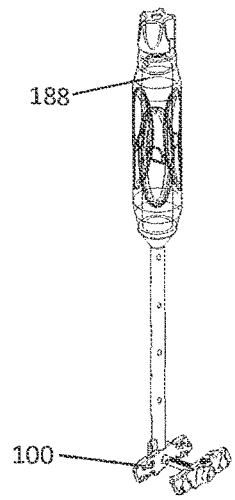
FIG. 13 A perspective view of a single shaft inserter holding an assembled spinous process plate fixation assembly shown in FIG. 1.
Figure 14:
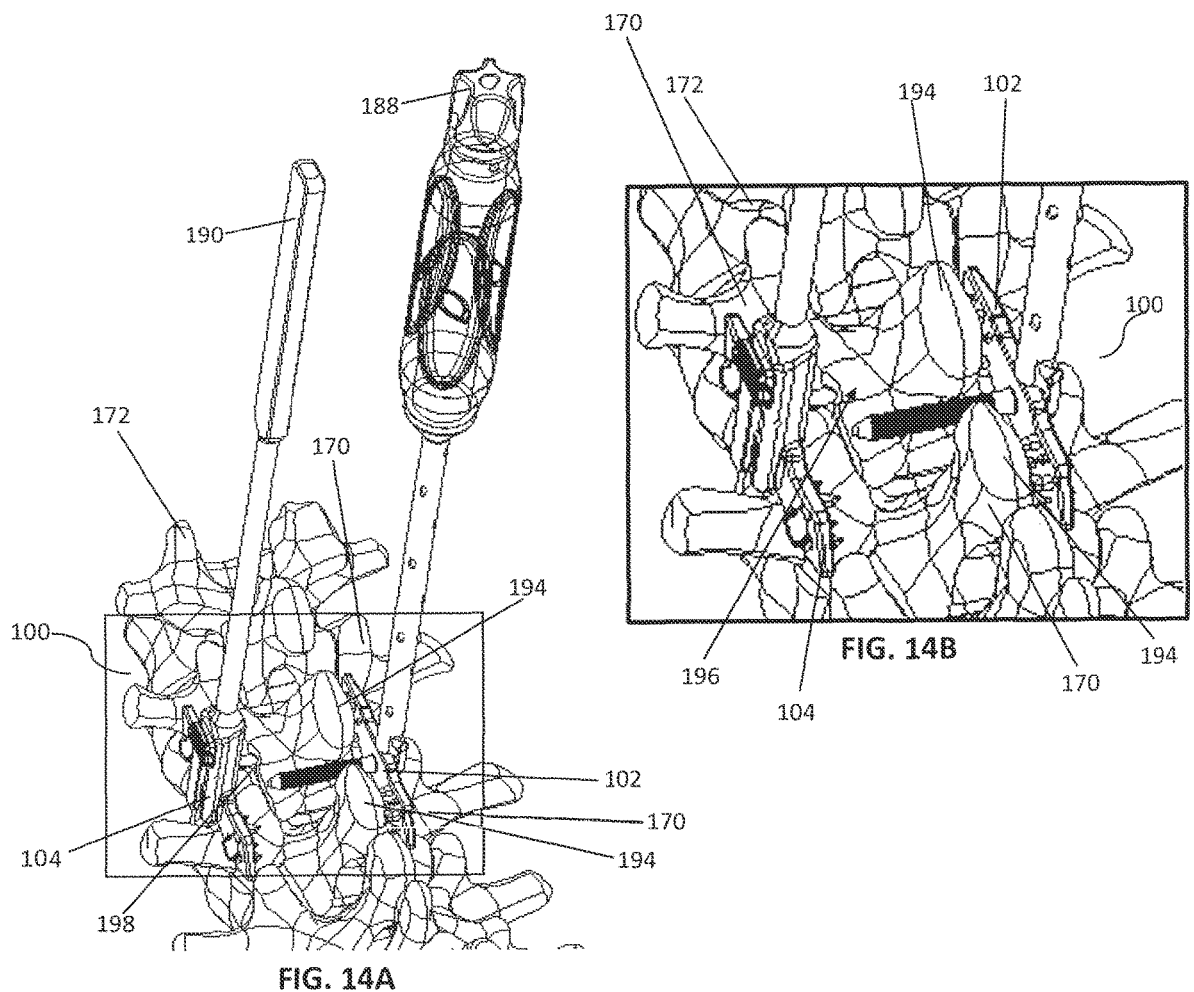
FIG. 14A A perspective view of a ligament sparing surgical technique showing a pin plate through a ligament with a lock plate being introduced into the surgical site with the single shaft inserter and a single locking tool.
FIG. 14B A magnified view of the pin plate and the lock plate in the ligament sparing surgical technique shown in FIG. 14A.

As shown in FIG. 13, a single shaft inserter 188 may cooperate with the assembly 100 to insert the lock pin 114 into the pin receptacle 112. FIG. 14A illustrates a single locking tool 190 to insert the threaded locking feature 158 into the threaded channel 136, being used with the single shaft inserter 188 while the assembly 100 is in-use during a spinal surgical procedure, such as a ligament sparing technique. In FIG. 14A, the pin plate 102 is through a ligament 198, and the lock plate 104 and the pivoting lock mechanism 126 are being introduced into the surgical site. FIG. 14B is an enlarged view of the assembly 100 of FIG. 14A.

Figure 15:
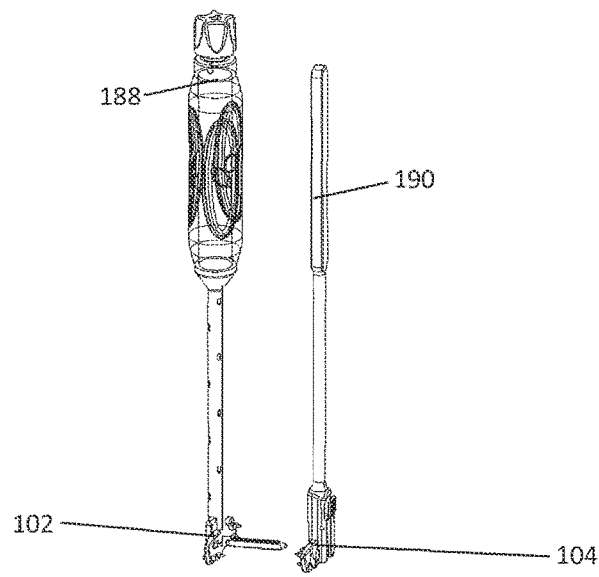
FIG. 15 A perspective view of the single shaft inserter and the single locking tool on the spinous process plate fixation assembly shown in FIG. 1 when using the ligament sparing surgical technique.
Figure 16:
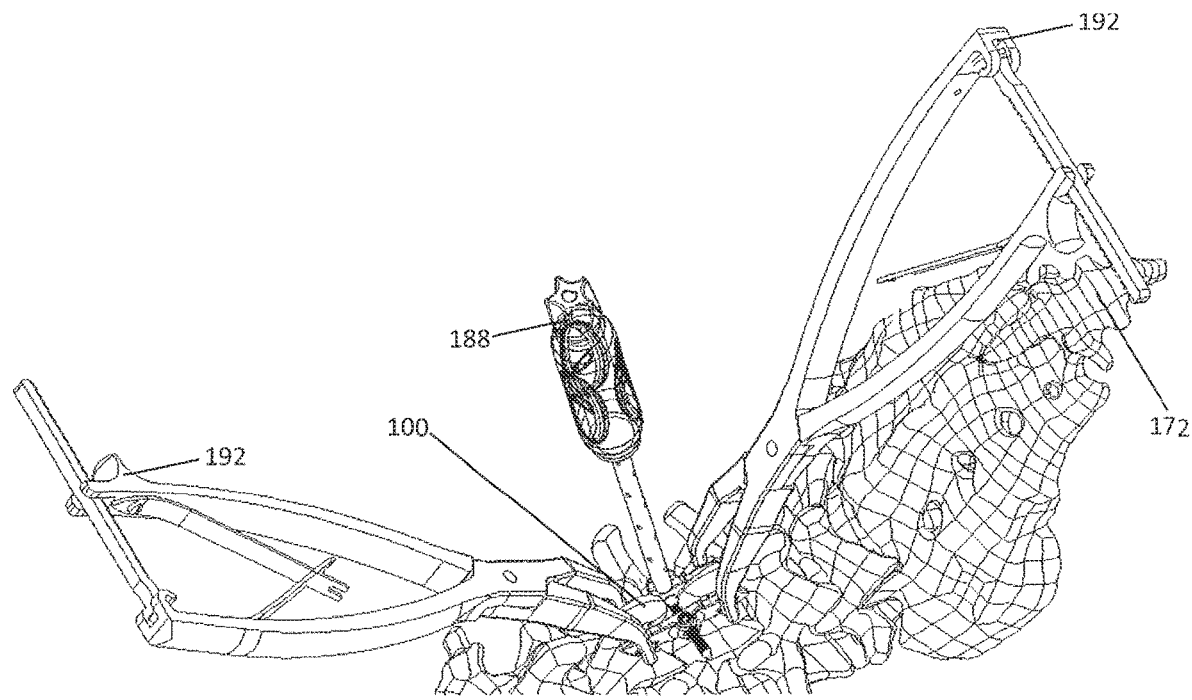
FIG. 16 A perspective view showing the assembly shown in FIG. 1 being compressed using simple compressors on a spine.

FIG. 15 illustrates the single shaft inserter 188 and the single locking tool 190 when using the ligament sparing technique. FIG. 16 illustrates the assembly 100 being assembled and compressed using a pair of simple compressors 192 in a spine 172.

In an embodiment, a kit is provided that includes the assembly 100. The kit may include the lock pin 114, the pin plate 102, the lock plate 104, the pivoting lock mechanism 126, and the connector shaft 128. The kit may include the threaded locking feature 158, the pivoting lock 142, and the lock flange 148. At least one instrument may be provided in the kit, the instrument selected from the group of: the combination inserter-compressor instrument 186, the single shaft inserter 188, the single locking tool 190, the simple compressor 192, and combinations thereof.

Figure 6:
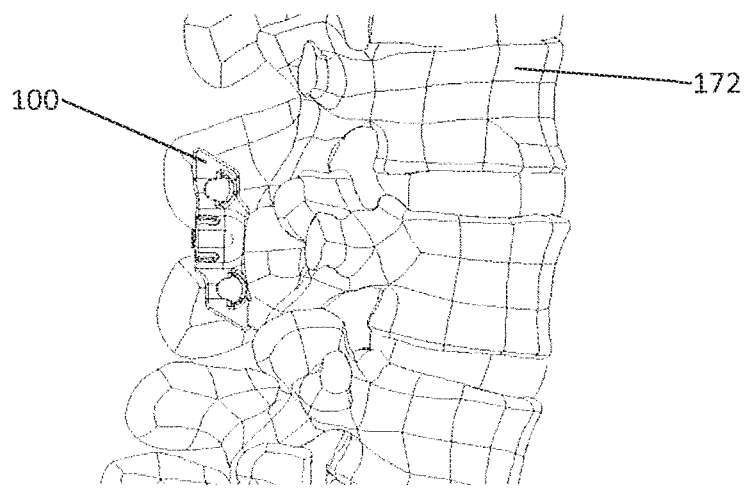
FIG. 6 A lateral view of the spinous process plate fixation assembly shown in FIG. 1 compressed to a spine in one orientation.
Figure 7:
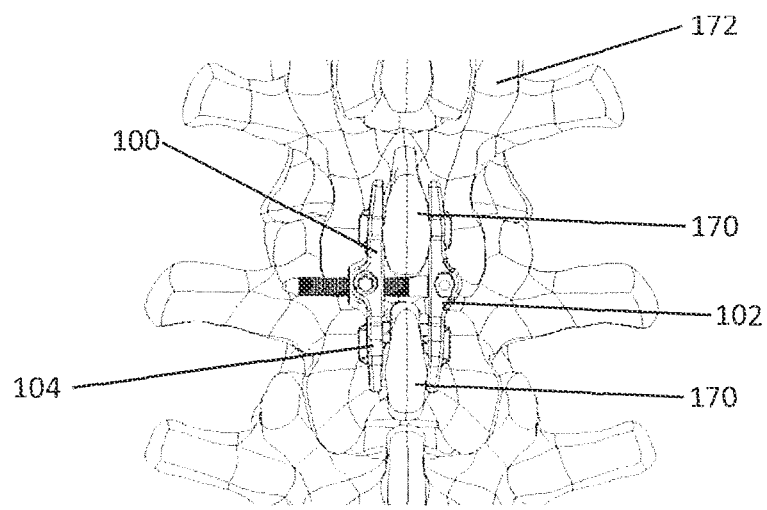
FIG. 7 A posterior view of the spinous process plate fixation assembly and spine shown in FIG. 6.
Figure 8:
FIG. 8 A perspective view of the spinous process plate fixation assembly and spine shown in FIG. 6.

A method of implanting and facilitating fixation between two spinal vertebrae is provided using the assembly 100 is provided. A posterior midline skin and muscle incision is made between two spinous processes 194 and is opened to the spinal vertebrae 170. A decompression is performed, and/or an interbody device (not shown) is placed in an intervertebral disc space 196, and the assembly 100 is placed on the lateral sides of adjacent spinous processes 194 at the treated level, ensuring the pluralities of spikes 110 and 124 on medial facing plates 102 and 104 are engaging bone. The plates 102 and 104 are compressed toward each other, and the pluralities of spikes 110 and 124 are pressed into the spinous processes 194. The lock plate 104 is then locked down using the pivoting lock mechanism 126. FIGS. 6, 7, and 8 illustrate the assembly 100 locked onto the spine 172.

Spinal fusion surgical procedures using the disclosed spinous process plate fixation assembly 100 are referred to as ligament sparing type procedures. Advantageously, because the present assembly 100 is separable and is able to be assembled in-situ, as shown in FIGS. 14A, 14B, and 15, the ligament 198 does not need to be removed to use the assembly 100, enabling the present assembly 100 optimal for less invasive surgical procedures than alternative procedures and devices. During a ligament sparing procedure using the presently disclosed assembly 100, the pin plate 102 is inserted to the spine 172 and aligned to the first lateral side of two adjacent spinous processes 194. The lock plate 104 is inserted to the spine 172 and aligned to the opposite lateral side of the two adjacent spinous processes 194. The plates 102 and 104 are then moved toward each other such that the connector shaft 128 is inserted through the second central aperture 120 in the lock plate 104 and into the pivoting lock 142. Upon engagement, the plates 102 and 104 are urged toward each other until the pluralities of spikes 110 and 124 are driven into the lateral sides of the adjacent spinous processes 194. The plates 102 and 104 are urged toward each other until a predetermined level of compression is reached, then the threaded locking feature 158 is engaged to secure the assembly 100 in the fixed position. The threaded locking feature 158 may be engaged, for example, by inserting it into the threaded channel 136 and rotating it so that the threads of the locking feature 158 and the channel 136 cooperate to drive the locking feature 158 into the channel 136. The instruments disclosed herewith allow separation and assembly through the interspinous ligament 198 without having to remove the ligament 198.

The assembly 100 may be constructed of any suitable materials, including biocompatible materials. Some embodiments of the assembly 100 are constructed of non-absorbable biocompatible materials. Specific examples of such suitable materials include titanium, alloys of titanium, steel, stainless steel, and surgical steel. The assembly 100, or parts thereof, could conceivably be made from non-metallic biocompatible materials, which include aluminum oxide, calcium oxide, calcium phosphate, hydroxyapatite, zirconium oxide, and polymers such as polypropylene. The plates 102 and 104 and respective pluralities of spikes 110 and 124 may be integrally formed.

Midline Spinous Process Allograft

As discussed above, the spinous process plate fixation assembly 100 can be used with an allograft, such as a midline spinous process allograft. A midline spinous process allograft 200 is provided herein. When posterior fixation is performed, such as posterior lumbar fusion or posterior lumbar interbody fusion, a postlateral fusion typically extends to the transverse process in order to lay allograft or autograft to create a fusion. However, the allograft 200 of the present disclosure allows for the creation of a fusion without extending past the facets, enabling a less invasive surgical procedure compared to alternatives.

Figure 17:
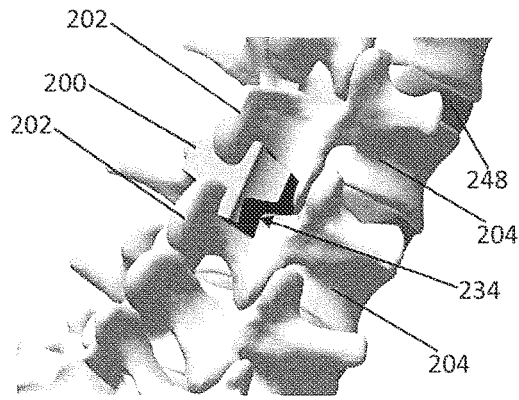
FIG. 17 A perspective view of an embodiment of a midline allograft placed between spinous processes of adjacent lumbar vertebrae.
Figure 18:
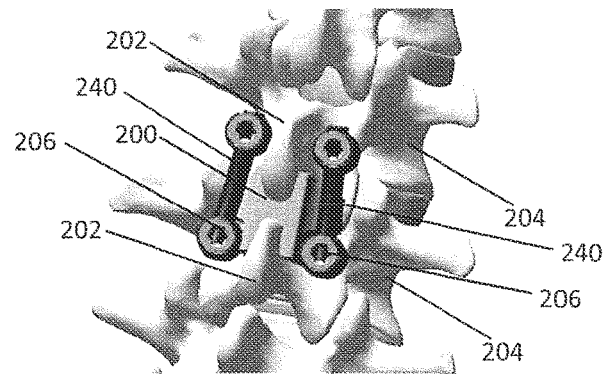
FIG. 18 A perspective view of the midline allograft of FIG. 17 with posterior fixation elements installed.

As shown in FIGS. 17 and 18, the allograft 200 is configured to be positioned between spinous processes 202 of lumbar and/or thoracic vertebrae 204 during a spinal fusion surgical procedure. As shown in FIG. 18, the allograft 200 can be used in conjunction with pedicle screw systems 206. The midline spinal allograft includes a body 208 having a lower side (i.e., distal side) 210 opposite of an upper side 212 (i.e., proximal side). The lower side 210 has a caudal groove 214 dimensioned to receive a cranial side of the lower spinous process 202. The upper side 212 has a cranial groove 216 dimensioned to receive a caudal side of the upper spinous process 202. The cranial groove 216 may have a cranial groove height 218 greater than a caudal groove height 220 of the caudal groove 214. The cranial groove 216 may have a cranial groove width 222 greater than a caudal groove width 224 of the caudal groove 214. The larger cranial groove 216 allows the allograft 200 to reach the lamina of the vertebra 204 of the spinous process 202, allowing for more, or enhanced, fusion. As shown in FIG. 17, the allograft 200 is positioned for an L2 to L3 vertebrae 204 fusion.

The midline spinal process allograft 200 includes two lateral wings 226, each wing 226 disposed on opposite sides of the body 208. At least two lower legs 228 are disposed around the caudal groove 214, and at least two upper legs 230 are disposed around the cranial groove 216. The lower legs 228 and upper legs 230 are disposed on opposite sides of the body 208 and are proximate to the wings 226. The lower legs 228 may taper inwardly toward the caudal groove 214 such that each of the legs 228 has a lower leg surface 250 shaped complementary to laminar for improved laminar contact.

Figure 19:
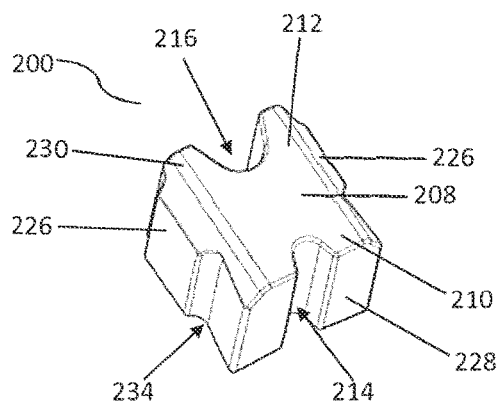
FIG. 19 A perspective view of an embodiment of a midline allograft.
Figure 20:
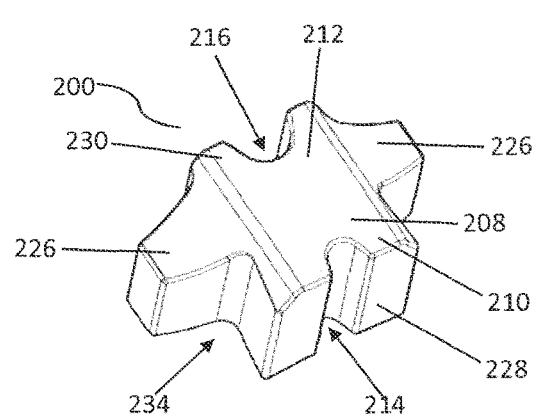
FIG. 20 A perspective view of another embodiment of a midline allograft.

The lateral wings 226 may be dimensioned to extend a distance that is further from the body 208 than a distance that the lower legs 228 extend, as shown in FIG. 20. In an alternate embodiment, shown in FIG. 19, the lateral wings 226 may be dimensioned to extend a distance that is proximal from the body 208 than a distance that the lower legs 228 extend. Advantageously, in embodiments of the allograft 200 having lateral wings 226 that extend a distance that is further from the body 208 than a distance that the lower legs 228 extend, the wider wings 226 are capable of extending to a facet joint 248 of the vertebrae 204, allowing an increased amount of scaffold to incorporate a bone fusion. Moreover, wider wings 226 allow the wings to go more anterior to allow rod passage of the rod 240 above the allograft 200.

In an embodiment of the midline spinal process allograft 200, the cranial groove 216 continuously tapers inwardly away from the upper legs 230 and toward a center 232 of the body 208. Similarly, the caudal groove 214 may continuously taper inwardly away from the lower legs 228 and toward the center 232 of the body 208.

The midline spinal process allograft 200 may have at least two caudal bone fixator spaces 234 dimensioned to receive a caudal bone fixator, such as the pedicle screw system 206. Each of the at least two caudal bone fixator spaces 234 is defined by the area between the lower legs 228 and the lateral wings 226. In an embodiment of the midline spinal allograft 200, the allograft 200 may be vertically symmetrical around a center plane 236.

The body 208 includes a top face 238 and lateral sides 244, the top face 238 and lateral sides 244 each forming a junction 242 dimensioned to receive a rod 240, such as the rod 240 of the pedicle screw system 206, shown in FIG. 18, positioned parallel to the junction 242. The junctions 242 may continuously curve from the top face 238 to the lateral sides 244 such that the junctions 242 are shaped complementary to the rod 240.

The allograft 200 may include a distal face 246 that continuously curves inwardly away from the lateral sides 244 and toward the center point 232 of the body 208. The distal face 246 may be dimensioned and shaped for spinal dura clearance after decompression of a spine 172 when the allograft 100 is in use in a subject. The shape and dimensions of the allograft 200, including the grooves 214 and 216 and the legs 228 and 230, allows enhanced compression to occur between the vertebrae.

The allograft 200 may be fully demineralized or partially demineralized, or used without any demineralization. The allograft 200 may be dimensioned to fit several different anatomies, such as that of an adult, child, male, or female human. In embodiments of the allograft 200 that are demineralized, the allograft 200 may fit a larger range of subject sizes that that of a mineralized allograft, increasing surgeon convenience and technique. A kit may be provided having a plurality of allografts 200, each having varying sizes so that a surgeon may select the optimal patient-specific allograft 200.

In yet another aspect, a method of producing a demineralized midline spinous allograft, such as the allograft 200 of the present disclosure, is disclosed herein. The method includes harvesting cancellous bone, cutting the harvested cancellous bone into a predetermined block size, weighing the cut cancellous bone, determining the cut cancellous bone has a mass density greater than a minimum mass density, shaping and sizing the cut cancellous bone to a predetermined shape and size to form a midline spinous allograft, washing the midline spinous allograft, demineralizing the midline spinous allograft in an acid, cleaning the demineralized midline spinous allograft, and packaging the cleaned demineralized midline spinous allograft. The packaging may include freezing drying or packaging in saline. In embodiments having packaging in saline, the graft is dried, and bone marrow aspirate is taken from a patient and soaked into the demineralized allograft.

The harvesting may from a source of cancellous bone such as a condyle of a femur bone of a human. The cancellous bone may be shaped with a manual machine, such as a hand router, or a computer-controlled cutting machine. The minimum mass density may be about 0.8 g/cm.sup.3. The acid may be hydrochloric acid. A plurality of demineralized midline spinous allografts using the method of demineralization disclosed herein. The plurality of demineralized would be produced having different predetermined shapes and sizes such that a surgeon can select a patient specific midline spinous allograft from the plurality of demineralized midline spinous allografts for use during spinal surgery of the patient.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 CFR 1.77 or otherwise to provide organizational queues. These headings shall not limit or characterize the invention(s) set forth herein.

What is claimed is:

1. A midline spinous process allograft, comprising:
a body including a lower side, an upper side opposite the lower side, a top face, a distal face opposite the top face, and a pair of lateral sides opposite one another;
two lower legs disposed on the lower side;
a caudal groove disposed between the two lower legs;
two upper legs disposed on the upper side;
a cranial groove disposed between the two upper legs;
a lateral wing disposed on each of the pair of lateral sides of the body and proximate to the two lower legs and two upper legs,
a junction disposed above each lateral wing, each junction extending from the top face to the distal face, wherein each junction is curved from the upper side to one of the lateral wings.

2. The midline spinous process allograft of claim 1, wherein the caudal groove is dimensioned to receive a cranial side of a lower spinous process.

3. The midline spinous process allograft of claim 1, wherein the cranial groove is dimensioned to receive a caudal side of an upper spinous process.

4. The midline spinous process allograft of claim 1, wherein the cranial groove is larger than the caudal groove.

5. The midline spinous process allograft of claim 1, wherein the caudal groove has a first height, and the cranial groove has a second height that is greater than the first height.

6. The midline spinous process allograft of claim 1, wherein the caudal groove has a first width, and the cranial groove has a second width that is greater than the first width.

7. The midline spinous process allograft of claim 1, wherein the two lower legs taper inwardly toward the caudal groove, such that the two lower legs form a shape that is complementary to a lamina of a vertebra.

8. The midline spinous process allograft of claim 1, wherein the lateral wing disposed on each of the pair of lateral sides extends a first distance from the body, and the two lower legs each extend a second distance from the body that is less than the first distance.

9. The midline spinous process allograft of claim 1, wherein the lateral wing disposed on each of the pair of lateral sides extends a first distance from the body, and the two lower legs each extend a second distance from the body that is greater than the first distance.

10. The midline spinous process allograft of claim 1, wherein the cranial groove tapers inwardly away from the two upper legs toward a center of the body.

11. The midline spinous process allograft of claim 1, further comprising two caudal bone fixator spaces that are dimensioned to receive a caudal bone fixator.

12. The midline spinous process allograft of claim 11, wherein the caudal bone fixator is a pedicle screw system.

13. The midline spinous process allograft of claim 11, wherein each of the two caudal bone fixator spaces are positioned between one of the two lower legs and one of the pair of lateral wings.

14. The midline spinous process allograft of claim 1, wherein each junction is dimensioned to complement an adjacent rod, the curved surface extending between the top face and a respective one of the pair of lateral sides.

15. The midline spinous process allograft of claim 1, wherein the distal face is configured to curve inwardly away from the pair of lateral sides toward a center of the body.

16. The midline spinous process allograft of claim 15, wherein the distal face is dimensioned for spinal dura clearance after decompression of a spine.

17. The midline spinous process allograft of claim 1, wherein the allograft is vertically symmetrical around a center plane.

18. The midline spinous process allograft of claim 1, wherein the allograft is fully demineralized or partially demineralized.

19. A kit comprising:
two or more midline spinous process allografts of claim 1, wherein each of the two or more midline spinous process allografts in the kit is sized and configured for use in a subject of a different size.

* * * * *